US012690887B2

(12) United States Patent
Newman et al.

(10) Patent No.: US 12,690,887 B2
(45) Date of Patent: Jul. 28, 2026

(54) DEVICES AND METHODS FOR PERFORMING WATER-AIDED ENDOSCOPY

(71) Applicant: Endeau, Inc., Escondido, CA (US)

(72) Inventors: Allen Newman, Rancho Santa Fe, CA (US); Sean Buxton, Providence, RI (US); Anthony DiBella, Franklin, MA (US); Kenneth F Binmoeller, Rancho Santa Fe, CA (US)

(73) Assignee: Endeau, Inc., Escondido, CA (US)

( * ) Notice: Subject to any disclaimer, the term of this patent is extended or adjusted under 35 U.S.C. 154(b) by 1136 days.

(21) Appl. No.: 16/929,057

(22) Filed: Jul. 14, 2020

(65) Prior Publication Data

US 2020/0337532 A1     Oct. 29, 2020

Related U.S. Application Data

(63) Continuation-in-part of application No. 16/775,219, filed on Jan. 28, 2020, now abandoned, which is a (Continued)

(51) Int. Cl.
| | |
|---|---|
| *A61M 35/00* | (2006.01) |
| *A61B 1/00* | (2006.01) |
| *A61B 1/012* | (2006.01) |
| *A61B 1/31* | (2006.01) |
| *A61B 17/32* | (2006.01) |

(Continued)

(52) U.S. Cl.
CPC ...... *A61B 17/3421* (2013.01); *A61B 1/00082* (2013.01); *A61B 1/00101* (2013.01); *A61B 1/00131* (2013.01); *A61B 1/00137* (2013.01); *A61B 1/00148* (2022.02); *A61B 1/012*

(2013.01); *A61B 1/31* (2013.01); *A61B 17/320016* (2013.01); *A61B 17/32056* (2013.01); *A61B 1/04* (2013.01)

(58) Field of Classification Search
CPC .............. A61B 1/31; A61B 17/320016; A61B 1/00137; A61B 1/012; A61B 1/00131
See application file for complete search history.

(56) References Cited

U.S. PATENT DOCUMENTS

| | | | | |
|---|---|---|---|---|
| 5,147,316 A | * | 9/1992 | Castillenti | .......... A61B 17/3421 |
| | | | | 604/174 |
| 7,276,075 B1 | * | 10/2007 | Callas | ................ A61B 17/3423 |
| | | | | 606/198 |
| 2006/0271095 A1 | * | 11/2006 | Rauker | .................... A61B 1/31 |
| | | | | 606/197 |

* cited by examiner

*Primary Examiner* — Anh T Dang
(74) *Attorney, Agent, or Firm* — Davison IP; Scott H. Davison

(57) ABSTRACT

An endoscopic plug for performing an endoscopic procedure includes an external housing and internal tubing for securing within a body cavity opening, the external housing including a plurality of support tabs to secure the external housing to an exterior of the body cavity opening, and the internal tubing including an expandable balloon on an outer surface for expanding within the body cavity to secure the plug within the body cavity. The support tabs, expandable balloon and other features help to create a sealed internal environment for performing water aided endoscopy ("WAE"). The endoscopic plug additionally includes an air passage within the internal tubing to inflate the expandable balloon, sloped edges adjacent to the support tabs to seal the external housing to an external opening of the body cavity, and a plurality of valves, seals and pumps which allow for the introduction and retention of liquid into the body cavity.

8 Claims, 19 Drawing Sheets

Related U.S. Application Data continuation of application No. 14/777,393, filed as application No. PCT/US2014/030568 on Mar. 17, 2014, now Pat. No. 10,542,871.

(60) Provisional application No. 61/801,427, filed on Mar. 15, 2013, provisional application No. 61/786,520, filed on Mar. 15, 2013.

(51) Int. Cl.
| | |
|---|---|
| *A61B 17/3205* | (2006.01) |
| *A61B 17/34* | (2006.01) |
| *A61H 9/00* | (2006.01) |
| *A61B 1/04* | (2006.01) |

100

SECTION A-A

112

112

SECTION A-A

DEVICES AND METHODS FOR PERFORMING WATER-AIDED ENDOSCOPY

CROSS-REFERENCE TO RELATED APPLICATIONS

This application is a continuation-in-part of U.S. application Ser. No. 16/775,219, filed Jan. 28, 2020, which is a continuation of U.S. application Ser. No. 14/777,393, filed Sep. 15, 2015, now U.S. patent Ser. No. 10/542,871, issued Jan. 28, 2020, which is a U.S. national phase filing of International Patent Application No. PCT/US2014/30568, entitled SYSTEMS, METHODS AND DEVICES FOR PERFORMING WATER AIDED ENDOSCOPY, which claims benefit of priority to U.S. Provisional Patent Application No. 61/801,427, filed Mar. 15, 2013, and U.S. Provisional Application No. 61/786,520, filed Mar. 15, 2013, the contents of the above applications are incorporated herein by reference in their entireties for all purposes.

BACKGROUND

Field of the Invention

The embodiments described herein are related to devices and methods for performing endoscopic procedures, and more particularly to an endoscopic plug with an expandable distal seal for performing water-aided endoscopy ("WAE").

Related Art

Endoscopy is a minimally invasive medical procedure where an endoscope is inserted into a body cavity in order to view the interior of the body cavity. If the body cavity has no orifice to the external environment, an opening must be created through the skin for insertion of the endoscope. If the body cavity has an existing orifice, such as the colon or esophagus, the endoscope can be inserted through the orifice without requiring a separate opening. Once the opening is created, a gas—either air or carbon dioxide—is inserted into the cavity to inflate the body cavity for better viewing by the endoscope. Although endoscopy may be used simply to view the body cavity for diagnostic purposes, one or more tools may be inserted into the body cavity at the same time in order to perform an interventional diagnostic or therapeutic procedure.

Water-aided endoscopy ("WAE") is a type of endoscopy where the body cavity is filled with water instead of a gas. WAE provides several benefits over gas insufflation, including less distention of the body cavity and image magnification, but also provides significant challenges. While some leakage of air in an endoscopic procedure is expected and does not cause problems, leakage of water from WAE can cause many problems during the procedure, as leaking water may interfere with an individual performing the procedure and must be cleaned up. In addition, many of the tools used during a normal endoscopic procedure may not be suitable for use in a fluidic environment or perform the same way in WAE even if they are suited for exposure to liquid.

SUMMARY

Embodiments described herein include an endoscopic plug for performing an endoscopic procedure, and more particularly an endoscopic plug with an expandable balloon on an internal portion of the plug located in a body cavity, and support tabs on an external portion of the plug in an external environment, both of which secure the plug into a body cavity opening between the external environment and the internal body cavity to create a sealed internal environment for performing water aided endoscopy ("WAE"). The endoscopic plug additionally provides a dedicated air passage within the tubing housing to inflate the expandable balloon, where the tubing otherwise forms a channel for insertion of specialized tools into the body cavity while maintaining the sealed environment, with the channel having a plurality of valves, seals and pumps for introducing and maintaining liquid in the body cavity. The external portion includes sloped edges around the tubing distal to the support tabs to more comfortably insert and secure the plug into the body cavity opening.

In one embodiment of the invention, an endoscopic plug comprises: an external housing disposed external to a body cavity opening, the external housing including a sealed opening for insertion of one or more tools into a primary channel disposed therein; an internal housing disposed within a body cavity and connected with the external housing such that the primary channel continues through the internal housing to a distal opening for insertion of the one or more tools into the body cavity; wherein the internal housing includes an expandable balloon disposed around an outer surface of the internal housing; and wherein the internal housing includes a secondary channel disposed within a housing wall for passage of air from an external source to the expandable balloon.

In another embodiment of the invention, a method for inserting an endoscopic plug for water-aided endoscopy comprises the steps of: inserting a semi-flexible tubing into a body cavity opening, the tubing defining a primary channel and having an expandable balloon annularly disposed thereon in a deflated configuration; positioning a distal end of an external housing against an external surface of the body cavity opening to seal the external housing into the body cavity opening; and inflating the expandable balloon into an inflated configuration to create an internal seal between the expandable balloon and a body cavity wall.

Other features and advantages of the present invention will become more readily apparent to those of ordinary skill in the art after reviewing the following detailed description and accompanying drawings.

BRIEF DESCRIPTION OF THE DRAWINGS

The structure and operation of the present invention will be understood from a review of the following detailed description and the accompanying drawings in which like reference numerals refer to like parts and in which.

DETAILED DESCRIPTION

Certain embodiments disclosed herein provide for devices used for performing water-aided endoscopy ("WAE"), including an endoscopic plug with an expandable balloon on an internal housing of the plug located in a body cavity, and support tabs on an external housing of the plug in an external environment, both of which secure the plug at a body cavity opening between the external environment and the internal body cavity to create a sealed internal environment for performing water aided endoscopy ("WAE"). The endoscopic plug additionally includes a semi-flexible tubing with a dedicated air passage to inflate the expandable balloon, tapered edges adjacent to the support tabs to more comfortably insert and secure the plug into the body cavity opening, and a plurality of valves, seals and pumps for introducing and maintaining liquid in the body cavity. The endoscopic plug additionally provides a channel within the semi-flexible housing for insertion of specialized tools designed to interface with the multi-functional plug for insertion into the body cavity while maintaining the seal.

As will be described further below, the expandable balloon, support tabs and tapered edges all provide improved mechanisms for sealing and securing the endoscopic plug within the body cavity opening. The expandable balloon secures the internal housing against a tissue wall inside the body cavity (such as a colon wall during a colonoscopy), while the support tabs secure the exterior housing against an outer surface of the body to prevent the plug from moving too far into the body cavity. The tapered edges provide an improved seal between the external housing and the body cavity opening while also providing a more comfortable insertion process during the endoscopic procedure.

The expandable balloon is configured to inflate at lower pressure while still providing a sufficient seal within the body cavity, due to its specific geometry that allows it to securely contact a tissue wall. In addition to the primary channel formed by the tubing and the external housing for passage of endoscopic tools, a separate secondary channel disposed within a wall of the tubing connects the expandable balloon with a pressurized air source that is connected with an opening in the external housing for inflation and deflation of the balloon.

After reading this description it will become apparent to one skilled in the art how to implement the invention in various alternative embodiments and alternative applications. However, although various embodiments of the present invention will be described herein, it is understood that these embodiments are presented by way of example only, and not limitation. As such, this detailed description of various alternative embodiments should not be construed to limit the scope or breadth of the present invention as set forth in the appended claims.

Figure 1:
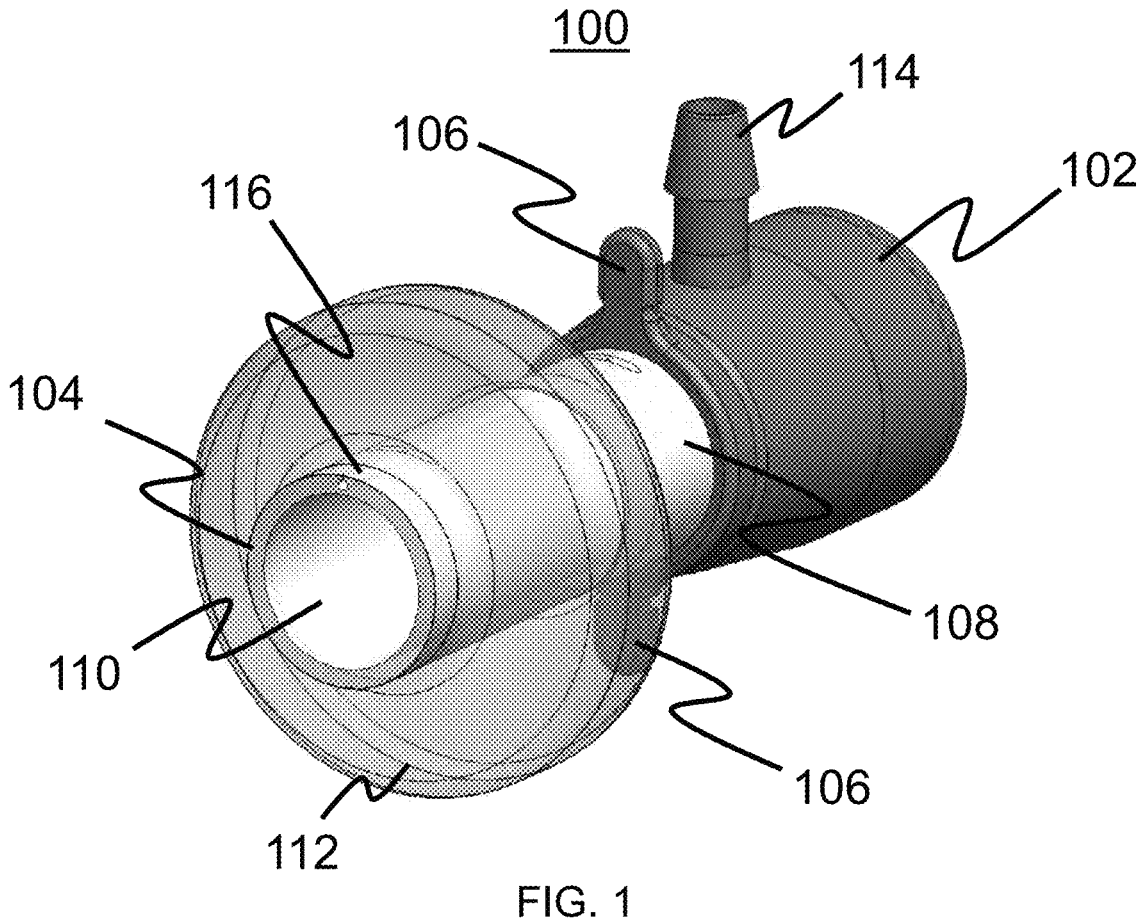
FIG. 1 is a perspective view illustration of an endoscopic plug with an internal housing and an external housing with an expandable balloon in an expanded configuration, according to an embodiment of the invention.

In one embodiment illustrated in FIG. 1, an endoscopic plug 100 comprises an external housing 102 and an internal housing 104, where the internal housing 104 is shaped to enter a body cavity opening and be secured therein, while the external housing 102 is shaped to reside outside of a body cavity opening and may be secured to an exterior surface surrounding a body cavity opening via one or more support tabs 106 which extend radially from a distal end of the external housing closest to its integration with the internal housing 104. The external housing may be generally cylindrically-shaped and form a primary channel therethrough—from a proximal end furthest from a body cavity to a distal end in communication with a similar channel extending the length of the internal housing. In this embodiment, a pair of support tabs 106 extend from the housing in opposing directions and may have dimensions suitable for securing into a gluteal cleft, for example when the plug is used for performing a colonoscopy. The external housing may also include a fluid port connector 114 for connecting with a fluid tube to provide fluid into the body cavity during a water aided endoscopy ("WAE") procedure.

The internal housing 104 may include a semi-flexible tubing 108 connecting with the external housing on one end and extending from the external housing and into the body cavity, where an inflatable balloon 112 is disposed around a distal end of the internal housing. In one embodiment, the inflatable balloon 112 is in communication with a secondary channel 116 disposed within the housing of the semi-flexible tubing 108 and further connected with a pressurized air source (as will be shown in detail below).

Figure 2A:
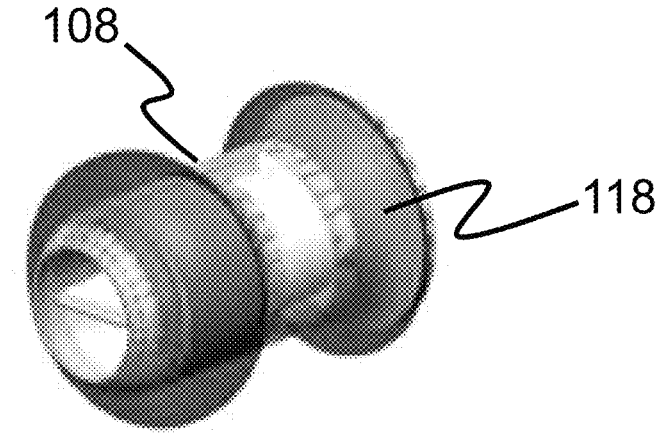
FIG. 2A is a perspective view illustration of an internal housing of the plug with a tapered proximal edge, according to an embodiment of the invention.
Figure 2B:
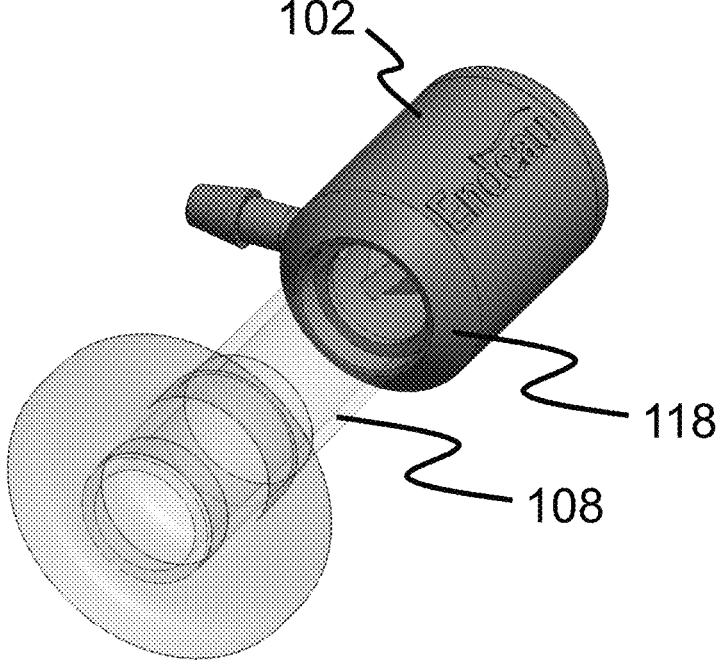
FIG. 2B is a perspective view illustration of the plug with the tapered proximal edge shown with the external housing, according to one embodiment of the invention.

FIG. 2A illustrates a perspective view of the plug illustrating a tapered edge 118 positioned between a distal end of the external housing 102 and a proximal end of the semi-flexible tubing 108, such that the tapering allows for a gradual increased friction-fit between the plug and the body cavity opening during insertion. FIG. 2B illustrates an additional embodiment of the plug with a larger external housing 102 which still includes a tapered edge 118 which tapers down to a diameter of the tubing 108.

Figure 3:
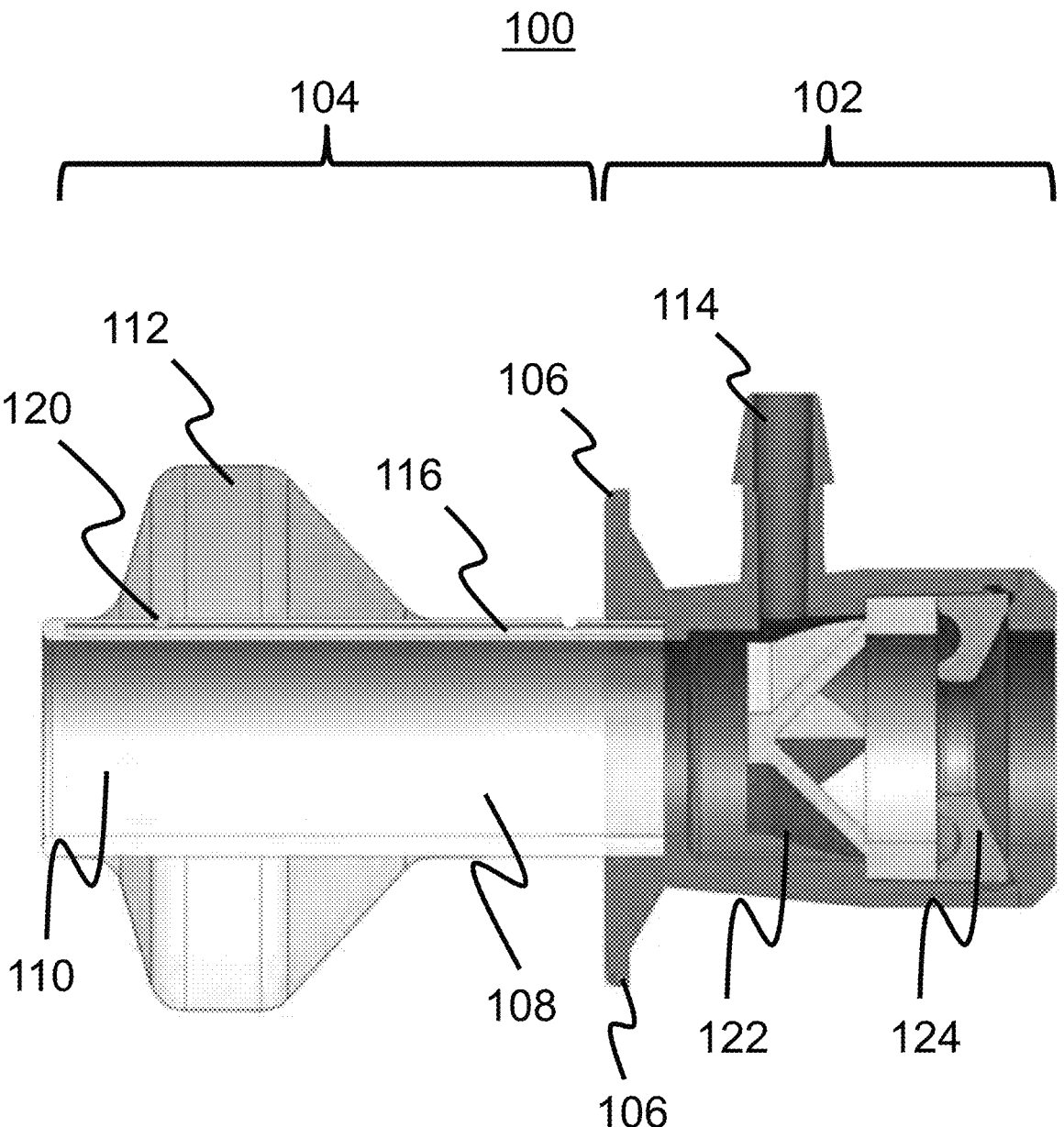
FIG. 3 is a cross-sectional side view illustration of the endoscopic plug, according to an embodiment of the invention.

FIG. 3 illustrates a side cross-sectional view of the plug 100, more clearly showing the delineation between the external housing 102 and internal housing 104. As has already been described above, the balloon 112 on the distal end of the internal housing 104 is in an inflated configuration due to passage of pressurized air from the inflation tube 116 disposed in the wall of the flexible tubing to the balloon 112 via an inflation tube opening 120 within the air-filled chamber. The cross-section also illustrates the length of the channel 110 which extends from the external housing 102 to the tubing 108 in the internal housing 104, where the external housing 102 incorporates a static seal 122 to allow endoscopic tools to pass through the channel and into the body cavity without letting fluid leak out of the channel 110. In this embodiment, the static seal 122 is a duckbill seal, although other types of seals may be used. In addition to the duckbill seal 122, a second dynamic seal 124 may be positioned proximal to the duckbill seal 122 to create an additional seal around the edge of an endoscopic tool being inserted into the plug.

Also illustrated in FIG. 3 is the location of the fluid port 114 extending out of the external housing 102 for connection with a fluid tube (see FIG. 6) that is used to fill the body cavity with fluid for WAE. The opening to the fluid port 114 is distal to the location of the duckbill seal 122 so that the fluid enters into the sealed environment of the channel 110. Finally, FIG. 3 additionally illustrates the location of the support tabs 106 at the distal-most position on the external housing 102, such that they are used to contact a body surface immediately around the body cavity opening in order to secure the plug 100 in the body cavity opening and prevent the plug from being pushed or pulled too far into the body cavity during an endoscopic procedure. Although the current embodiment envisions two support tabs 106 extending in opposing directions, as few as one, or more than two, may be utilized to properly secure the plug in the body cavity opening.

Figure 4:
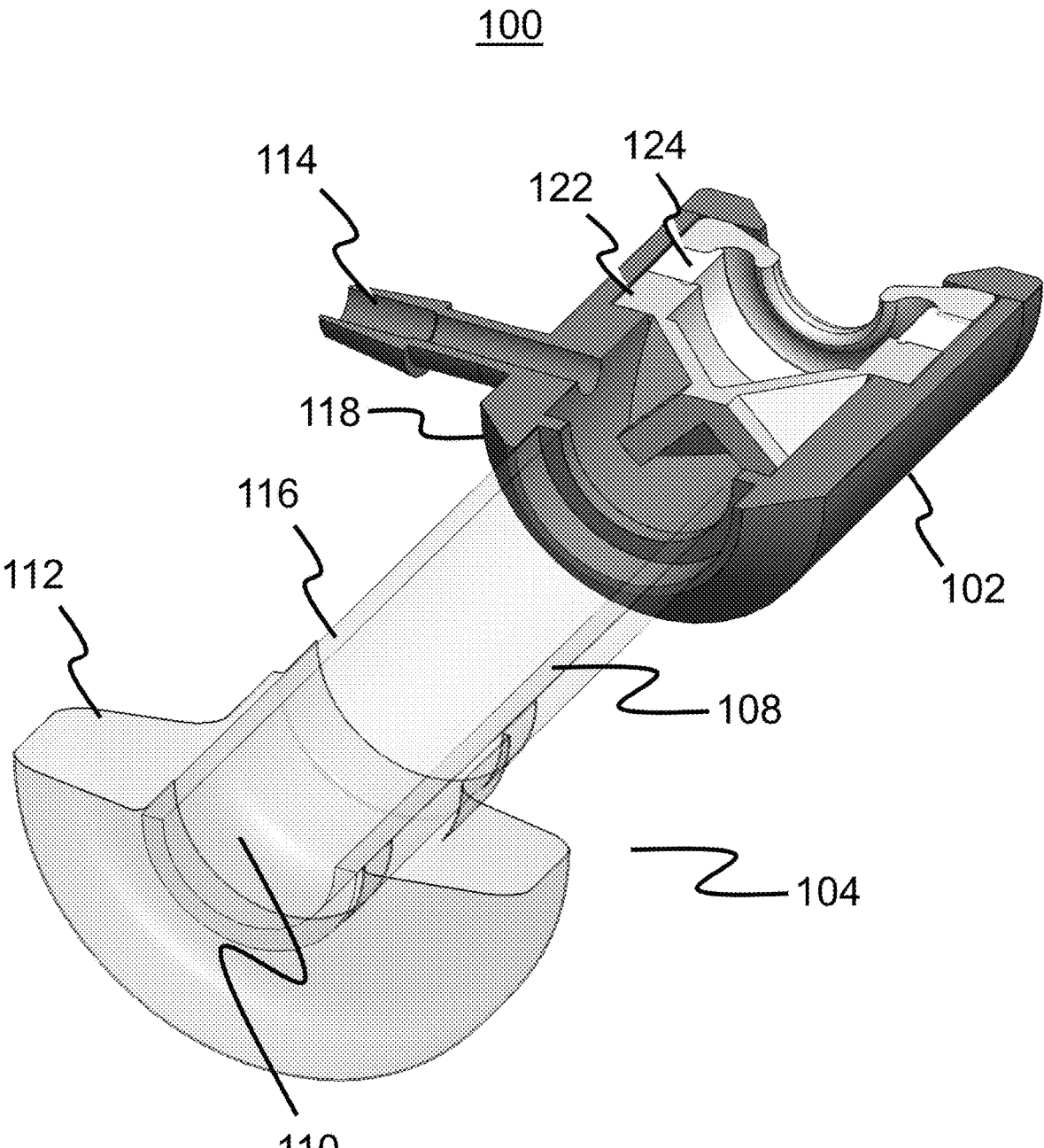
FIG. 4 is a cross-sectional perspective view illustration of the endoscopic plug, according to an embodiment of the invention.

FIG. 4 illustrates a cross-sectional perspective view of one embodiment of the plug 100, providing an additional illustration of the position and location of the semi-flexible tubing 108 with the inflation tube 116 disposed therein. This embodiment also illustrates how the distal end of the external housing may include a tapered end 118 to allow the housing to more comfortably and securely fit into the body cavity opening. The tapered end 118 would taper the diameter of the external housing 102 from a first diameter that is necessarily wider than the internal housing 104 to a second diameter similar to that of the internal housing 104 so that the tapered end 118 of the external housing 104 would more accurately match the anatomical shape of a body cavity opening and create a better seal between the body cavity opening and the plug 100. Although not shown herein, the support tabs 106 would be positioned immediately proximal to the tapered end 118 such that the external housing would begin tapering down to the diameter of the tubing 108 immediately after the support tabs 106.

Figure 5A:
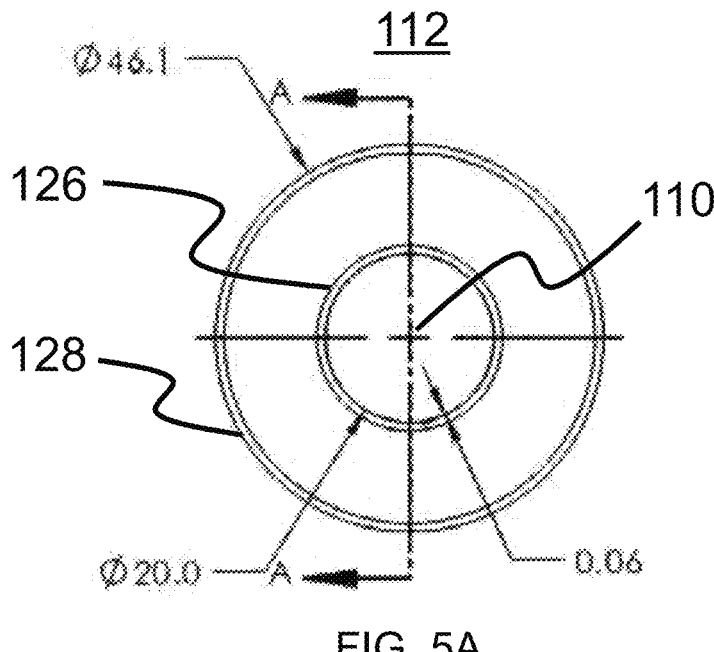
FIG. 5A is a cross-sectional front view of the expandable balloon, according to an embodiment of the invention.
Figure 5B:
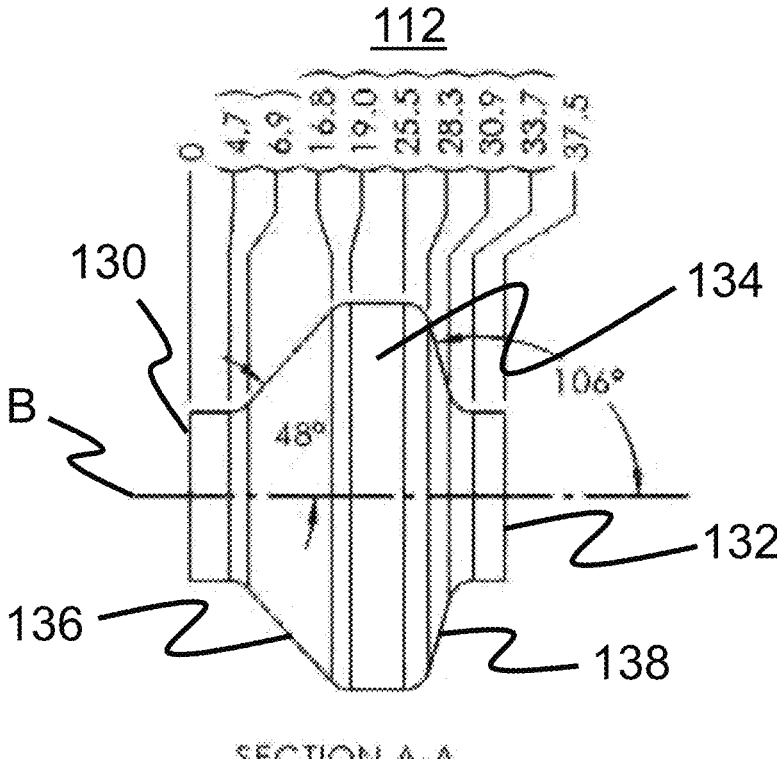
FIG. 5B is a cross-sectional side view of the expandable balloon taken along the A-A line in FIG. 5A, according to an embodiment of the invention.

The shape of the balloon 112 also aids in securing the plug within the body cavity when the balloon is inflated to contact a body cavity wall. FIG. 5A illustrates a front view of one embodiment of the expandable balloon 112 showing the channel opening 110, an inner diameter 126 surrounding the channel 110 and an outer diameter 128 representing the inflated configuration of the balloon 112. FIG. 5B is a cross-sectional side view of the expandable balloon taken along the A-A line in FIG. 5A, which illustrates a proximal end 130 and a distal end 132 with inner diameters 126 that are secured to the tubing 108 (not shown), as well as the bulbous central portion 134 which is configured to expand to the outer diameter 128 and contact a body cavity wall.

As shown by the side view in FIG. 5B, the balloon 112 tapers sharply along a distal slope 138 from the central portion 134 to the distal end 132 which corresponds to the distal end of the internal housing 104 of the plug 100 and the channel opening 110. In contrast, the balloon 112 tapers gradually along a proximal slope 136 from the central portion 134 to the proximal end 130 that corresponds to the proximal end of the internal housing 104 which is attached with the external housing 102. The gradual tapering of the proximal slope 136 is designed to allow easier removal of the plug in the event that the balloon 112 does not deflate, while the sharp tapering of the distal slope 138 is designed to provide as much surface area in the bulbous central portion 134 of the balloon that will contact the body tissue wall to create a better seal and prevent movement of the plug and leakage of fluid toward the body cavity opening. In this illustration, the gradual slope of the proximal slope 136 has an angle of approximately 48 degrees relative to the axial line B running through the center of the balloon, while the sharp slope of the distal slope 138 has an angle of approximately 106 degrees relative to the axial line.

One advantage to the balloon 112 of the present embodiment is that it may be inflated at a relatively low pressure to achieve the desired geometry described above. In one embodiment, the balloon may be fully inflated using a pressure of approximately 40-55 cubic centimeters (cc). The balloon 112 may be formed of a flexible material such as silicone or polyurethane in order to provide the specific shape geometry needed.

Figure 6:
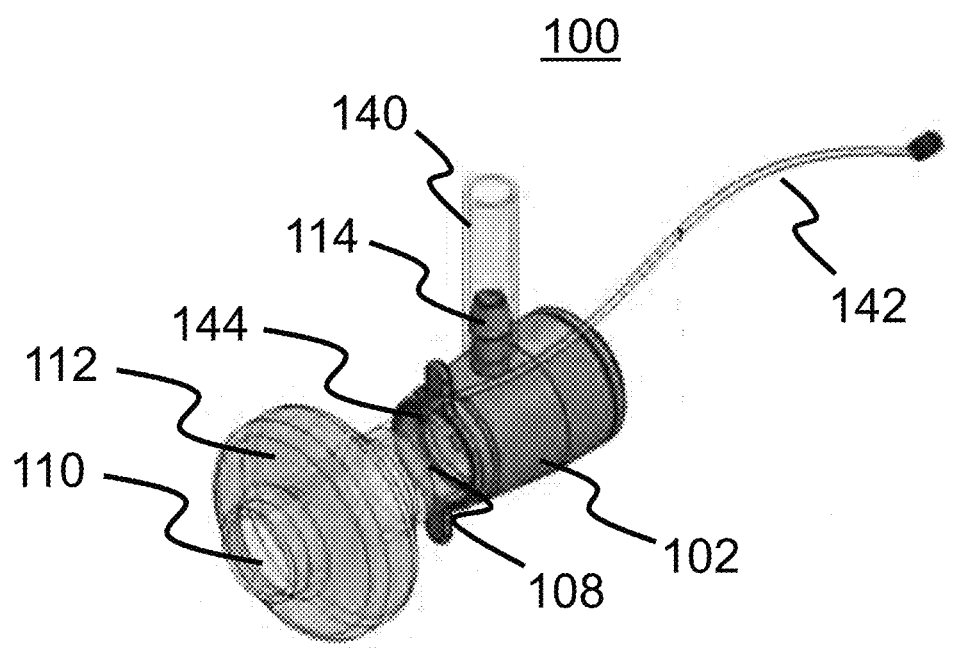
FIG. 6 is a perspective view illustration of the endoscopic plug connected with a balloon inflation tube and a fluid mitigation tube, according to one embodiment of the invention.

FIG. 6 is a perspective view illustration of the endoscopic plug 100 with a fluid mitigation tube 140 secured over the fluid port 114 to provide fluid into the channel 110 and the body cavity. FIG. 6 additionally illustrates a balloon inflation tube 142 which passes into the opening in the external housing 102 and connects with the inflation tube 116 of the tubing 108 to provide air for inflating and deflating the balloon 112. Although not illustrated here, the balloon inflation tube 142 may also be configured with a pressure sensor or a simple inflation indicator which provides a visual indication that the balloon 112 is inflated or deflated, or provides a numerical pressure value to indicate how inflated or deflated the balloon 112 may be.

Figure 7:
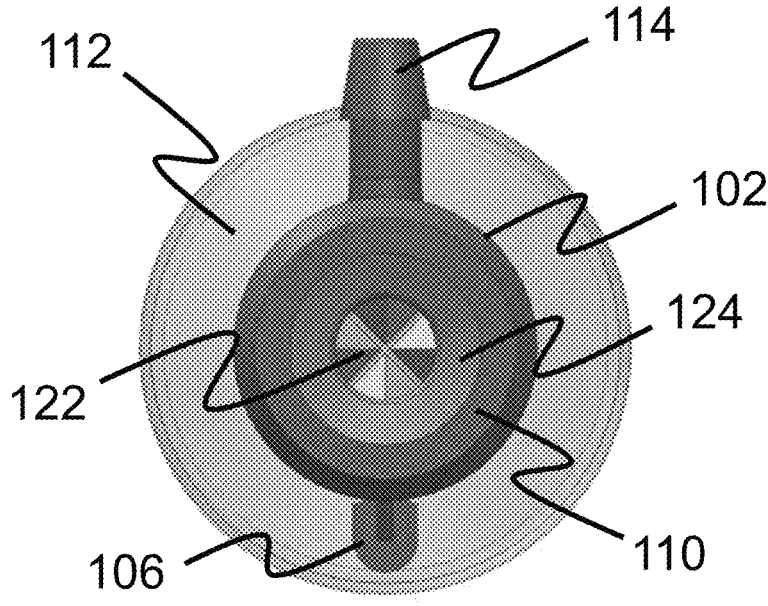
FIG. 7 is a rear view illustration of the opening of the plug in the external housing, according to one embodiment of the invention.

FIG. 7 is a rear view illustration of the opening of the plug as viewed from the external housing, according to one embodiment of the invention. This view provides an indication of the overall diameter of the external housing 102 relative to the inflated configuration of the balloon 112, along with an indication of the relative position of the support tab 106 and fluid port 114. Finally, in viewing the opening in the external housing into the channel 110, the diameter of the dynamic seal 124 and the closure of the duckbill seal 122 are visible.

Figure 8:
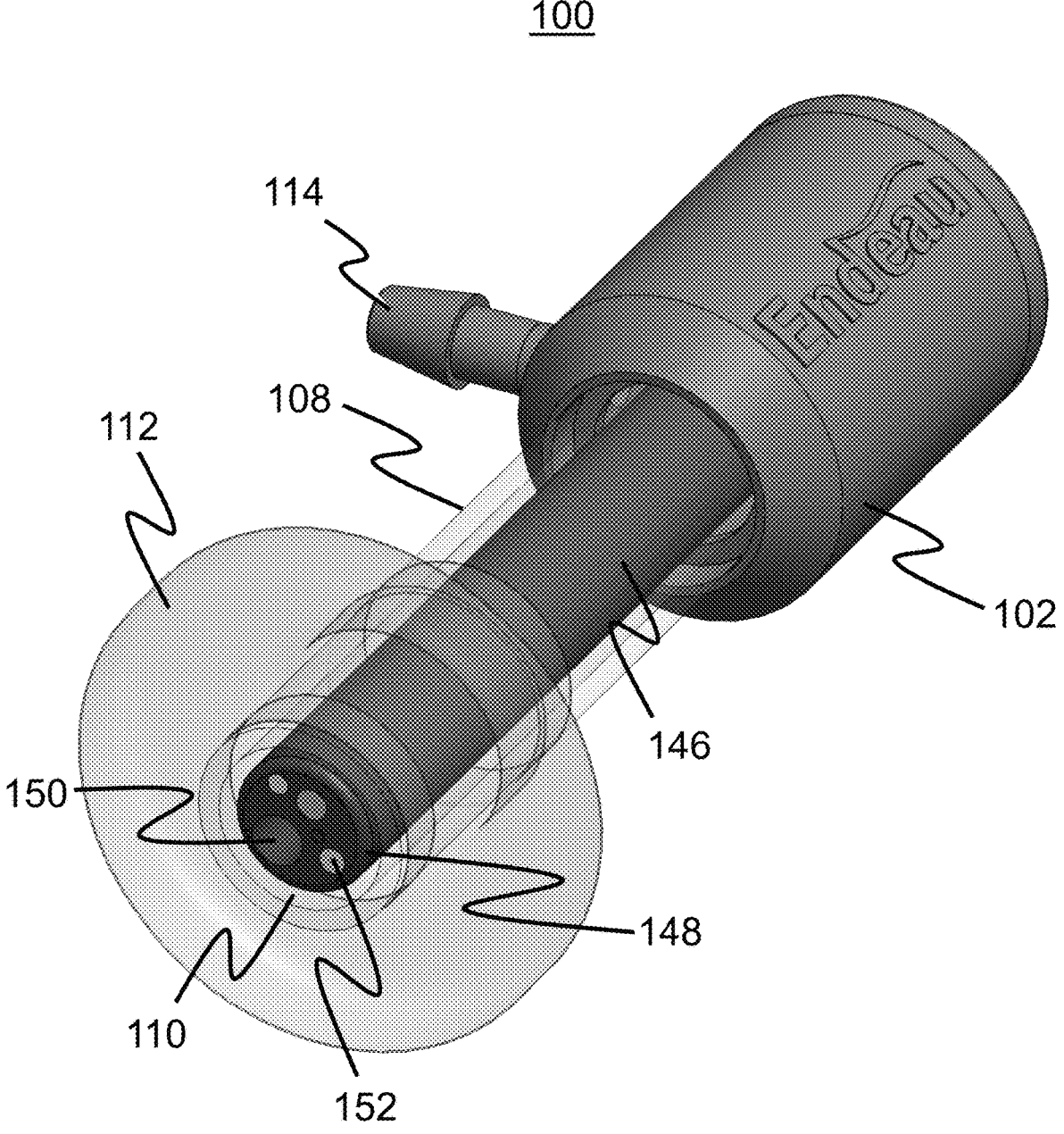
FIG. 8 is a perspective view illustration of the endoscopic plug with an endoscopic tool inserted therethrough, according to one embodiment of the invention.

Once the plug 100 is secured in the body cavity opening and the balloon 112 is inflated, an endoscopic tool 146 may be inserted through the channel and into the body cavity, as illustrated in FIG. 8. In this embodiment, the endoscopic tool 146 includes a variety of features at a distal end 148 which protrudes into the body cavity, such as an opening 150 for an additional tool and a plurality of sensors and lights 152.

Figure 9:
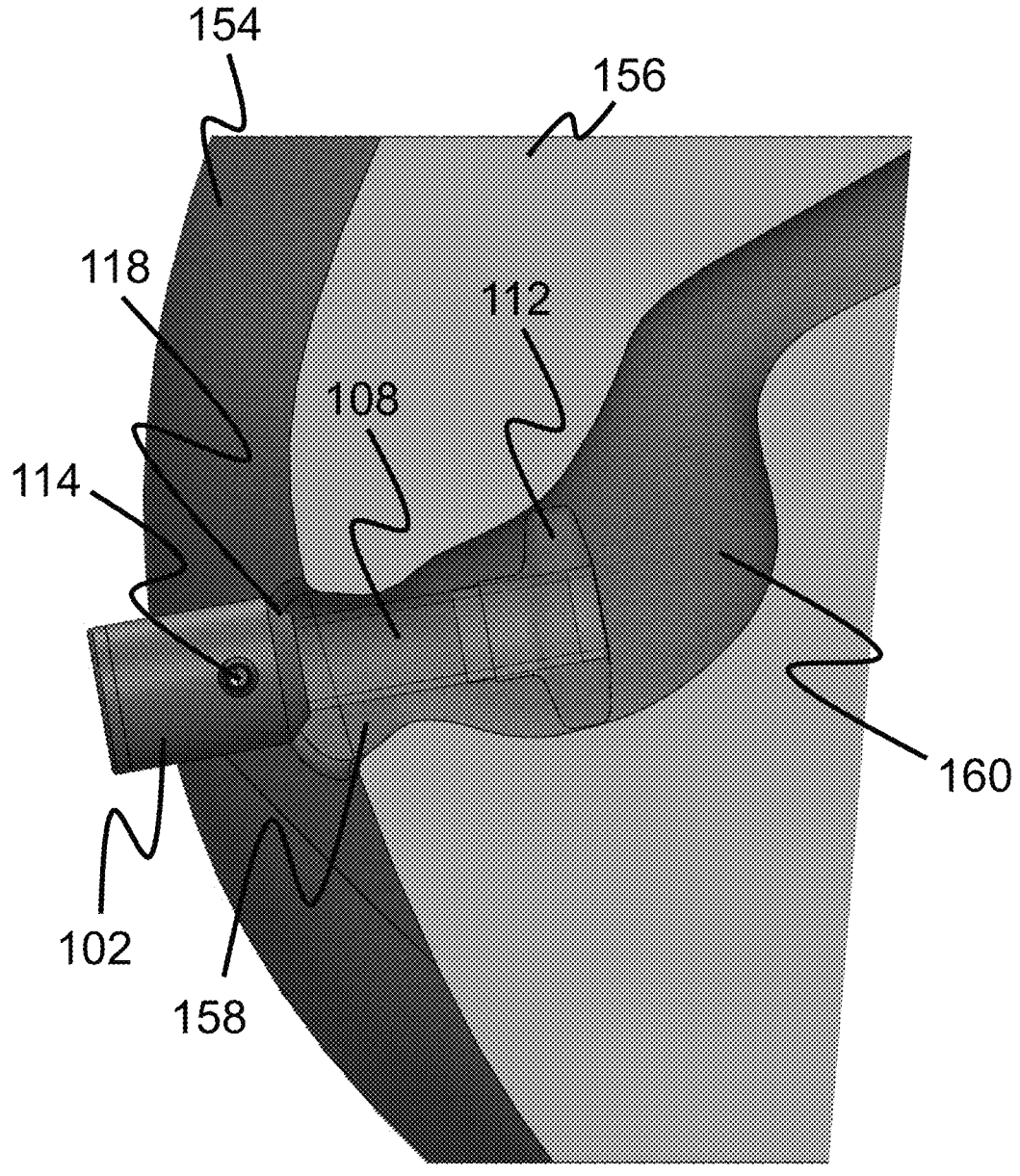
FIG. 9 is a side view illustration of the endoscopic plug after insertion into a body cavity, according to one embodiment of the invention.

FIG. 9 illustrates the plug in the inflated configuration during insertion through an outer surface 154 of a body 156 via a body cavity opening 158 and into a body cavity 160. The external housing 102 resides substantially outside of the body cavity opening 158 and will eventually be positioned to completely fill the opening 158 to create a seal between the distal, tapered end 118 of the external housing and the opening 158. Inside the body cavity 160, the balloon 112 has been inflated and is now in direct contact with the walls of the body cavity to create an additional seal that will prevent fluid that is eventually pushed into the cavity 160 from leaking back toward the body cavity opening 158. Thus, the plug creates two sealed areas between the body cavity and the plug in order to ensure that fluid will not leak out during WAE.

Figure 10A:
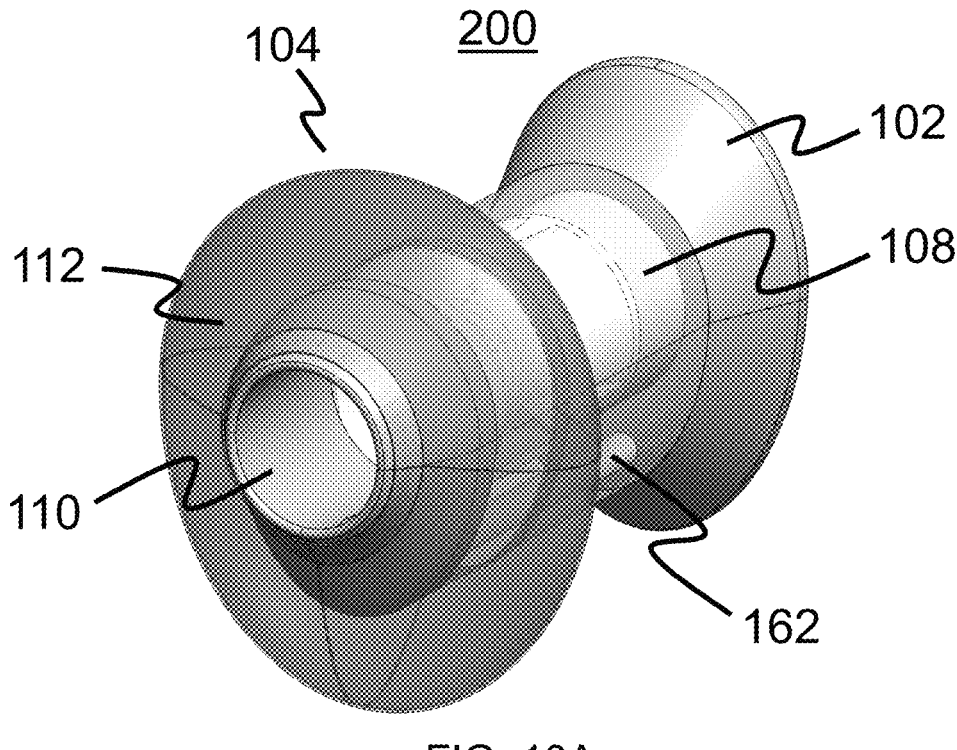
FIG. 10A is a perspective view illustration of an alternate endoscopic plug design with an expandable balloon in an expanded configuration, according to an embodiment of the invention.
Figure 10B:
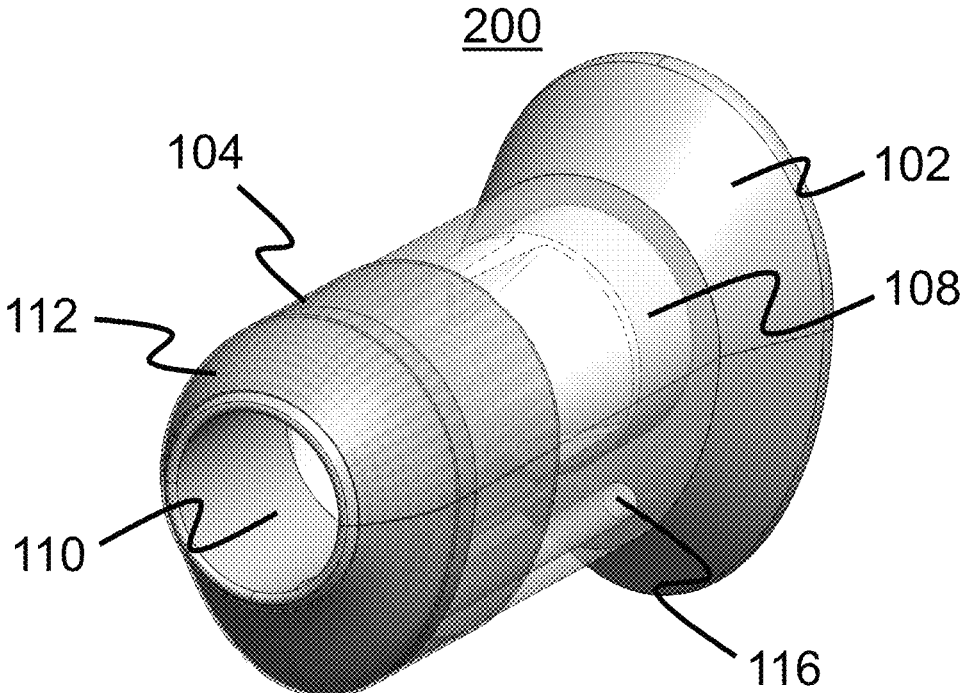
FIG. 10B is a perspective view illustration of the alternate endoscopic plug design with the expandable balloon in a deflated configuration, according to an embodiment of the invention.

FIG. 10A and FIG. 10B are perspective view illustrations of an alternate endoscopic plug 200 with a reduced profile external housing 102 and a fluid tube 162 separate from the semi-flexible tubing 108 for sending fluid into the body cavity. The fluid tube 162 and primary tubing 108 are both contained with a larger profile internal housing 104. FIG. 10A illustrates the alternate plug with the expandable balloon 112 in an expanded configuration, while FIG. 10B illustrates the alternate endoscopic plug design with the expandable balloon 112 in a deflated configuration, according to an embodiment of the invention. FIG. 10B illustrates how the deflated balloon 112 can be reduced to maintain essentially the same profile and diameter of the internal housing 104. In this embodiment, the external housing 102 is primarily tapered outward from the connection with the tubing 108 in order to fit within the body cavity opening.

Figure 11A:
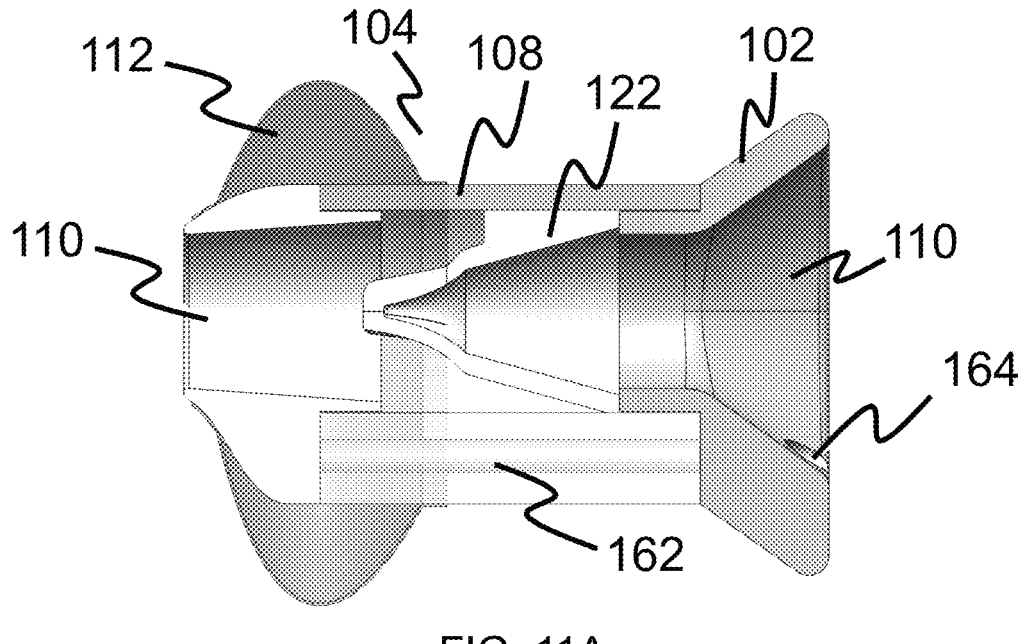
FIG. 11A is a cross-sectional view illustration of the alternate endoscopic plug design with a separate fluid tube housing and an integrated distal seal, according to an embodiment of the invention.
Figure 11B:
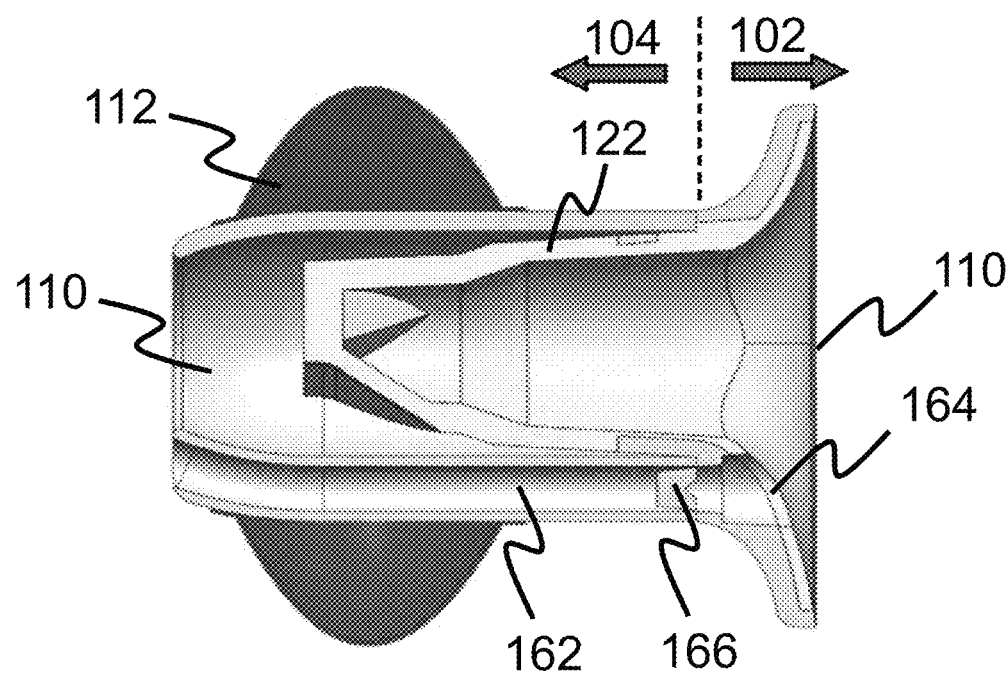
FIG. 11B is a cross-sectional view of the alternate endoscopic plug design with a further alternate fluid tube design, according to an embodiment of the invention.

FIG. 11A is a cross-sectional view illustration of the alternate endoscopic plug design more clearly illustrating the separate fluid tube 162 positioned below the primary tubing 108 that defines the channel 110. Furthermore, due to the reduced profile of the external housing 102, only a single static seal 122 is provided and is positioned substantially within the internal housing 104. The fluid tube 162 has a proximal fluid opening 164 on the internal surface of the channel 110 for connection with a fluid source. FIG. 11B more clearly illustrates the delineation between the external housing 102 and internal housing 104, and further illustrates an additional alternative configuration for the fluid tube 162 where it is incorporated immediately adjacent to the primary tubing 108. In one embodiment, a separate seal 166 may be incorporated into the inflation tube 116 for maintaining and regulating the fluid within the body cavity.

Figure 12:
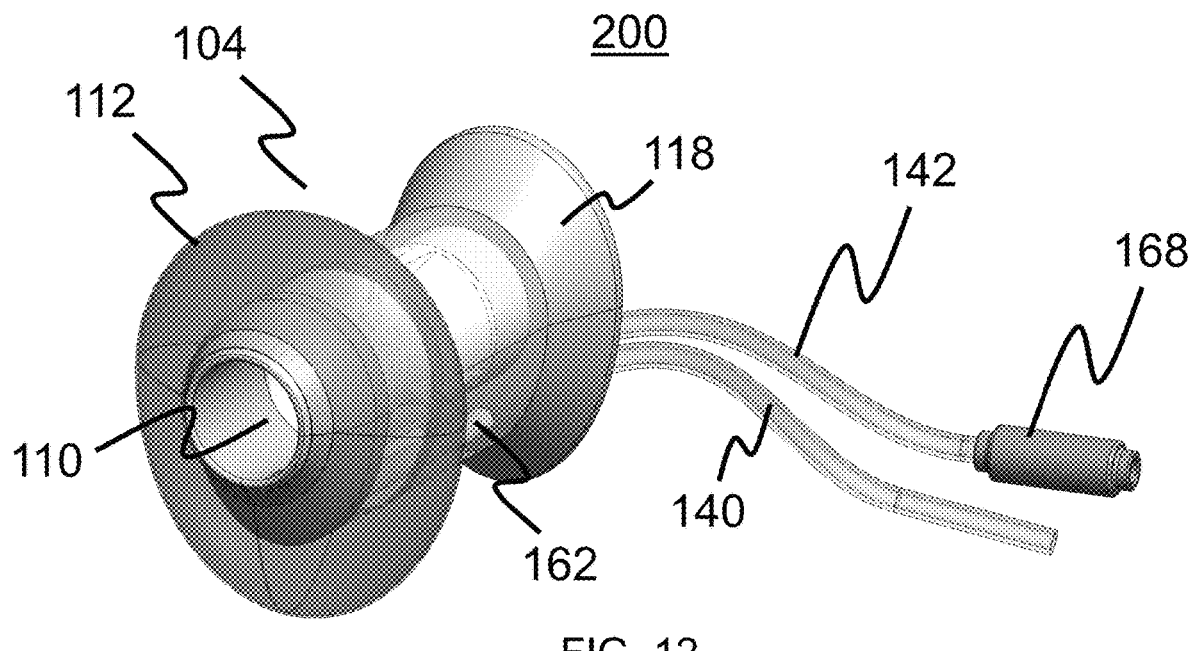
FIG. 12 is a perspective view illustration of the alternate endoscopic plug design with the separate fluid tube housing connected with the a fluid mitigation tube extending from the channel opening, according to one embodiment of the invention.

FIG. 12 is a perspective view illustration of the alternate endoscopic plug design 200 including the previously-described connected balloon inflation tube 142 as well as the fluid mitigation tube 140 connected with the fluid tube 162 and extending from the channel opening, according to one embodiment of the invention. As previously described, the balloon inflation tube 140 may also include a pressure sensor 168 indicating the level of pressure or amount of inflation of the balloon 112.

Figure 13:
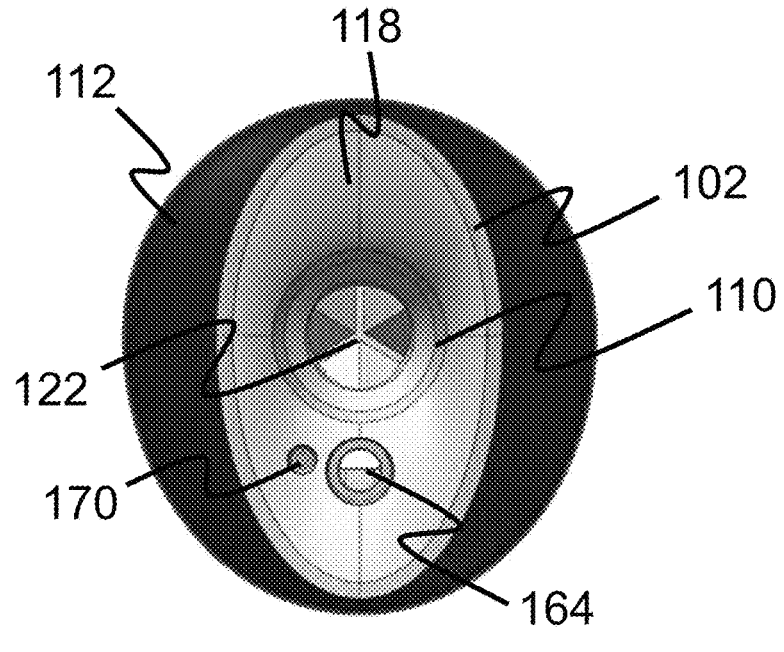
FIG. 13 is a rear view illustration of the opening of the plug in the external housing, according to one embodiment of the invention.

FIG. 13 is a rear view illustration of the opening of the plug in the external housing 102, illustrating the primary channel 110 and duckbill seal 122, but with the separate proximal fluid opening 164 and inflation opening 170 for connecting with a pressurized air source. Additionally, the larger tapered slope 118 of the external housing 102 is shown in comparison with the overall diameter of the balloon 112, particularly in comparison with the previous embodiment in FIG. 7.

Figure 14A:
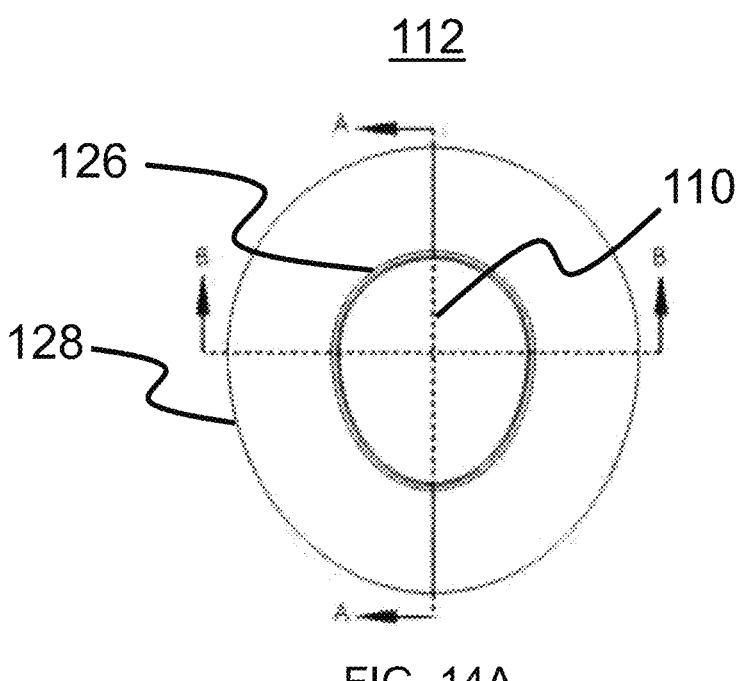
FIG. 14A is a cross-sectional side view of the expandable balloon, according to an embodiment of the invention.
Figure 14B:
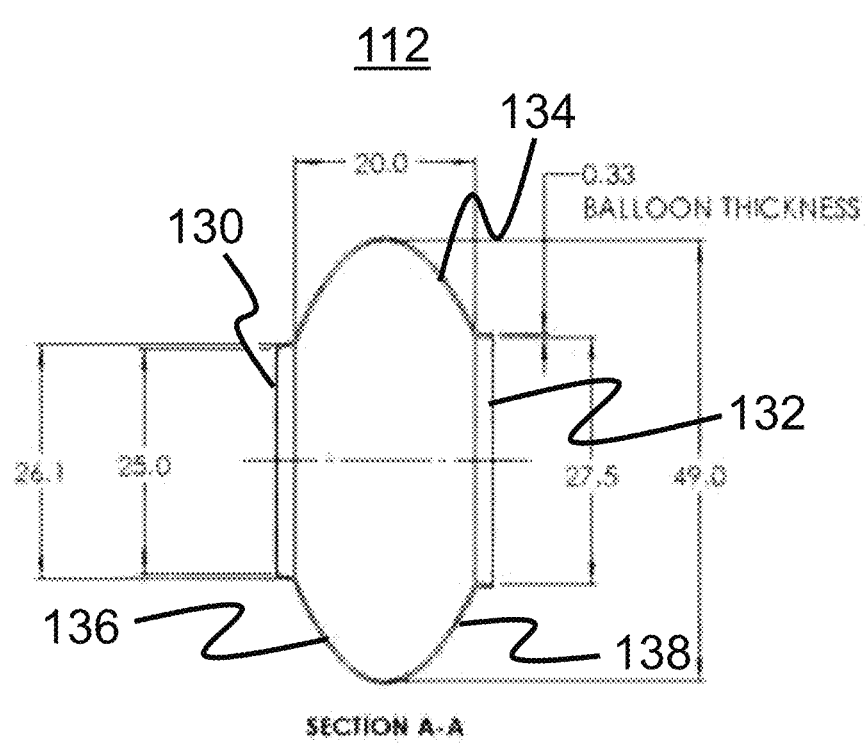
FIG. 14B is a cross-sectional side view of the expandable balloon taken along the A-A line in FIG. 14A, according to an embodiment of the invention.

FIG. 14A is a front view of the balloon 112 used for the alternate plug design in FIG. 10A, which has a more oval shape due to the larger internal housing 104 required to incorporate the separate fluid tube 162 into the design. The balloon 112 still has an internal diameter 126 shaped to fit the internal housing with the channel 110 protruding therethrough, and an external diameter 128 once the balloon 112 has been inflated. As seen in FIG. 14B by the cross-sectional side view of the expandable balloon 112 taken along the A-A line in FIG. 14A, the balloon 112 has a bulbous central portion 134 with tapered proximal slopes 136 and distal slopes 138 which taper down to their respective proximal end 130 and distal end 132. In this embodiment, the angle of the tapered slopes is identical on both proximal and distal sides, although the balloon 112 can be shaped similarly to that of the previous embodiment as well.

Figure 15:
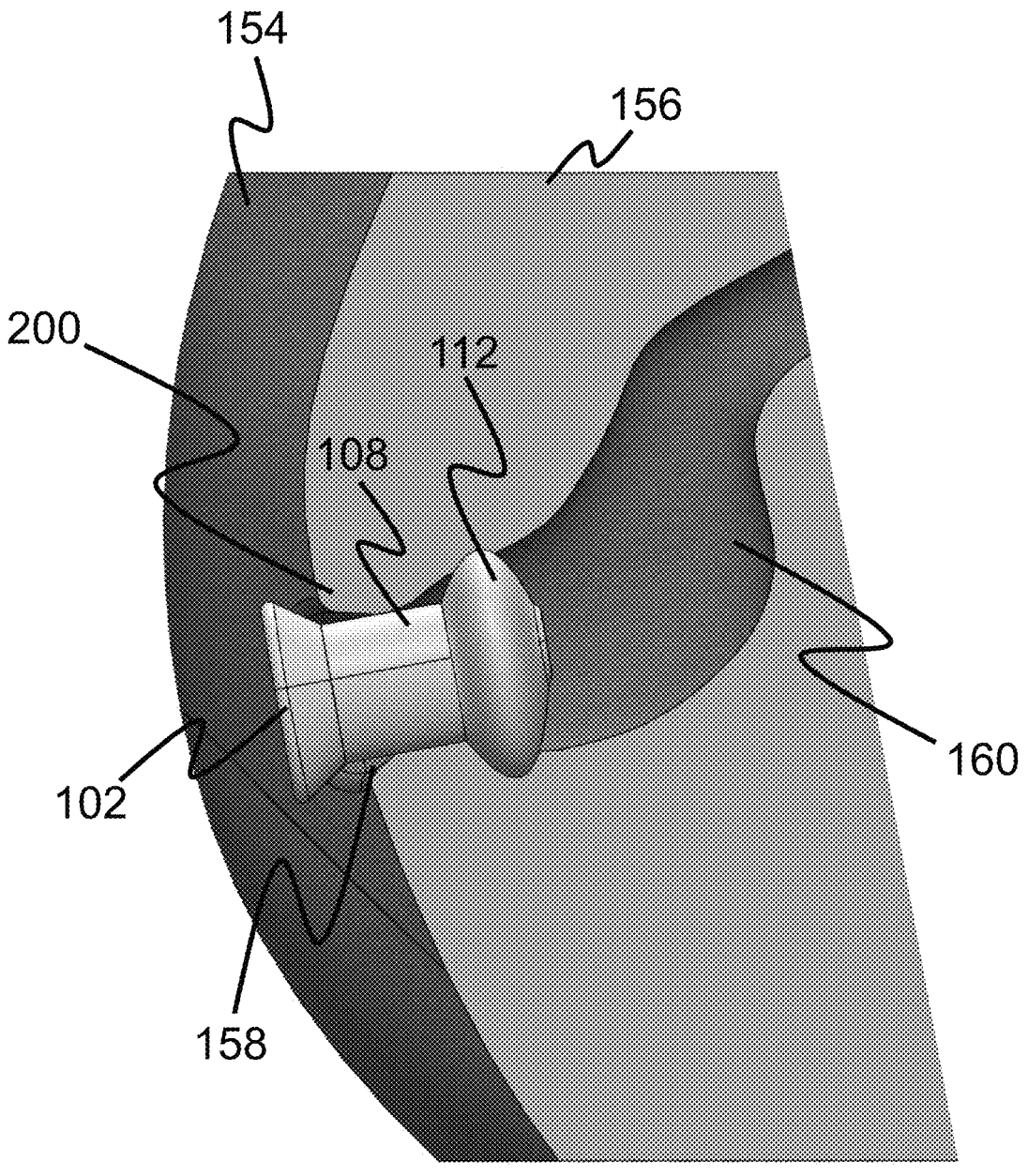
FIG. 15 is a side view illustration of the endoscopic plug after insertion into a body cavity, according to one embodiment of the invention.

FIG. 15 is a side view illustration of the alternate endoscopic plug design 200 after insertion into the body cavity 160 through an exterior body surface 154 of a body 156 via a body cavity opening 158. The balloon 112 is shown in the inflated configuration and secured to the walls of the body cavity 160, while the reduced profile external housing is substantially encompassed within the body cavity opening 158 for a secure fit.

Slidable Mount

Figure 16:
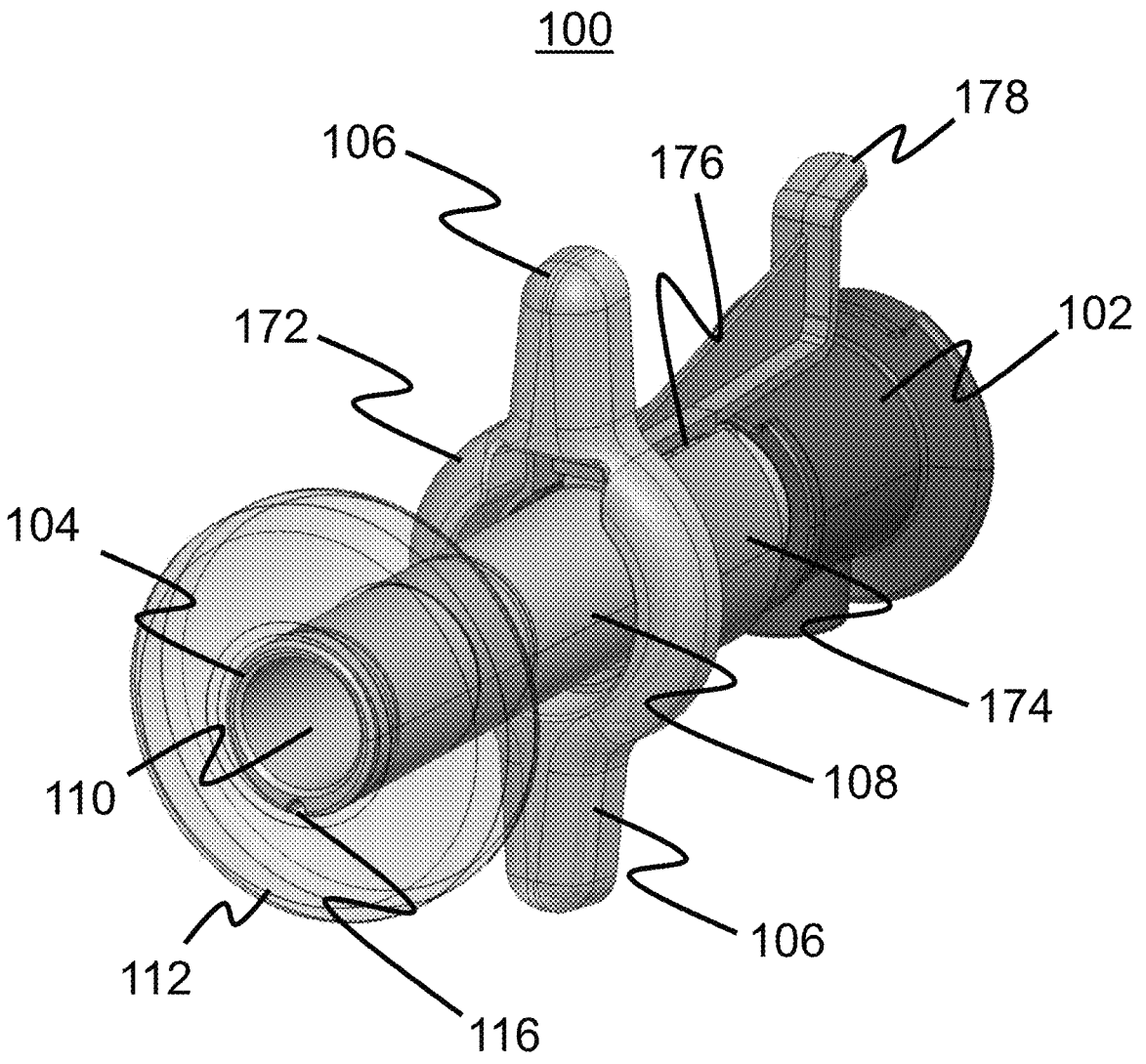
FIG. 16 is a perspective view illustration of an endoscopic plug with a slidable mount, according to one embodiment of the invention.

In one embodiment illustrated in FIG. 16, the endoscopic plug may be configured with a slidable mount 172 which secures the plug 100 into the anal cavity along with the balloon 112. The slidable mount 172 may be anatomically-shaped in a substantially rounded configuration with support tabs 106 extending in opposing directions along a vertical axis for insertion into the intergluteal cleft. The slidable mount is connected with a mount housing 174 surrounding the primary tubing 108 on the external housing portion 102 of the plug. The mount housing 174 is configured to slide across the primary tubing to push the slidable mount 172 up against the anus and intergluteal cleft and secure the plug against the anus.

Figure 17A:
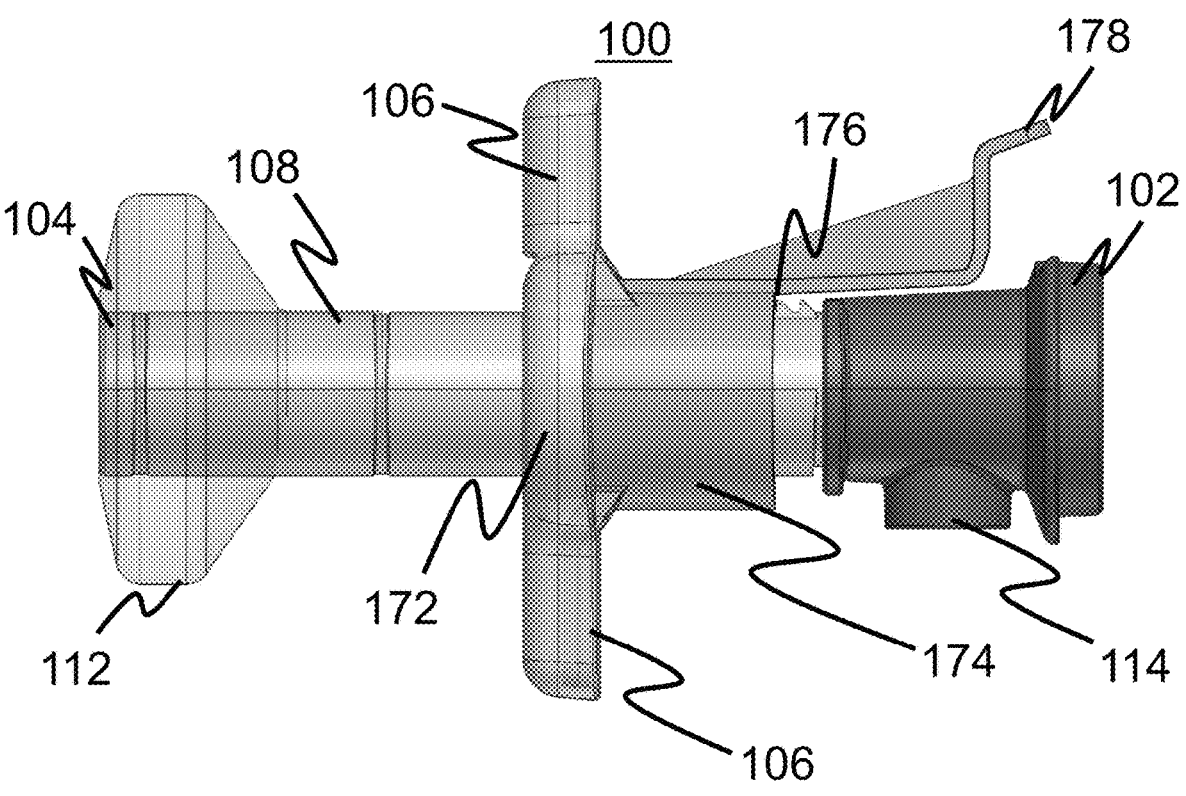
FIG. 17A is a side view illustration of the endoscopic plug with the slidable mount, according to one embodiment of the invention.
Figure 17B:
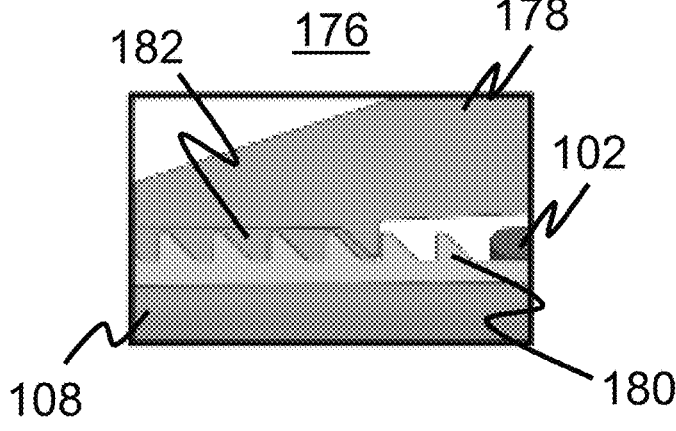
FIG. 17B is a detail view of a rachet locking mechanism for the slidable mount, according to one embodiment of the invention.

As shown in FIG. 17A, the mount housing 172 is configured with a ratchet locking system 176 including a ratchet locking tab 178 which a user can actuate to move the slidable mount 172 toward the anus, then release so that tube teeth 180 on the primary tubing 108 interface with tab teeth 182 on the ratchet locking tab 178 to lock the slidable mount 172 in place, as shown in FIG. 17B.

Figure 18:
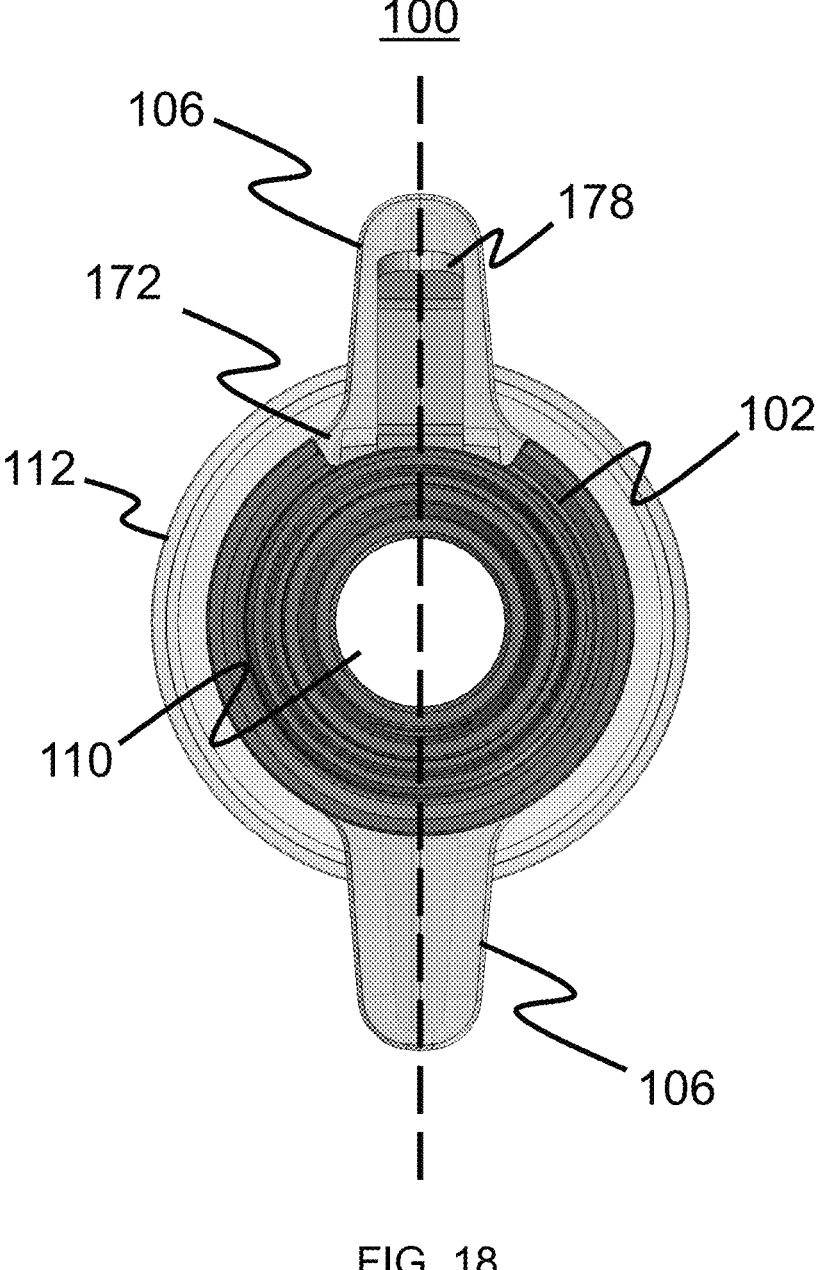
FIG. 18 is a rear view illustration of the slidable mount endoscopic plug, according to one embodiment of the invention.

FIG. 18 is a rear view illustration of the slidable mount endoscopic plug 100, illustrating the shape of the mount 172 with support tabs 106 relative to the diameter of the balloon 112 and channel 110. The intergluteal axis is represented by the dotted line bisecting the plug, illustrating how the support tabs 106 are shaped to secure the plug into the anus and intergluteal cleft. The ratchet locking tab 178 is also shown.

As with the previously described embodiments, the slidable mount 172 may be configured from a flexible or compressible material such as a soft silicone/TPE.

Double Balloon

Figure 19:
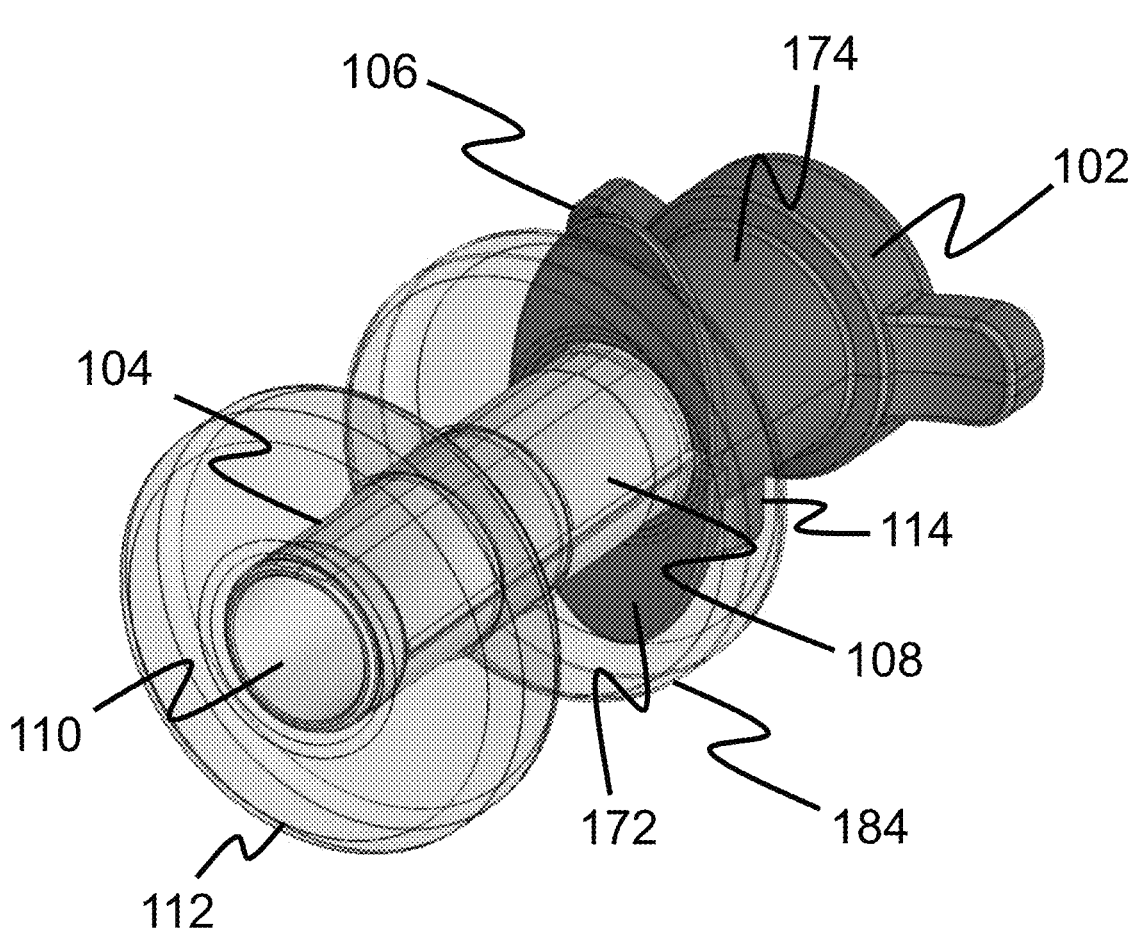
FIG. 19 is a perspective view illustration of an endoscopic plug with a slidable mount and two expandable balloons, according to one embodiment of the invention.

FIG. 19 is a perspective view illustration of one embodiment of endoscopic plug 100 with a slidable mount 172 and a second expandable balloon 184 immediately distal to the slidable mount which serves to securely and comfortably retain the plug 100 in the anus. The mount housing 174 in this embodiment is actuated by support tabs 106 placed at the proximal end of the plug 100.

Figures 20, 21:
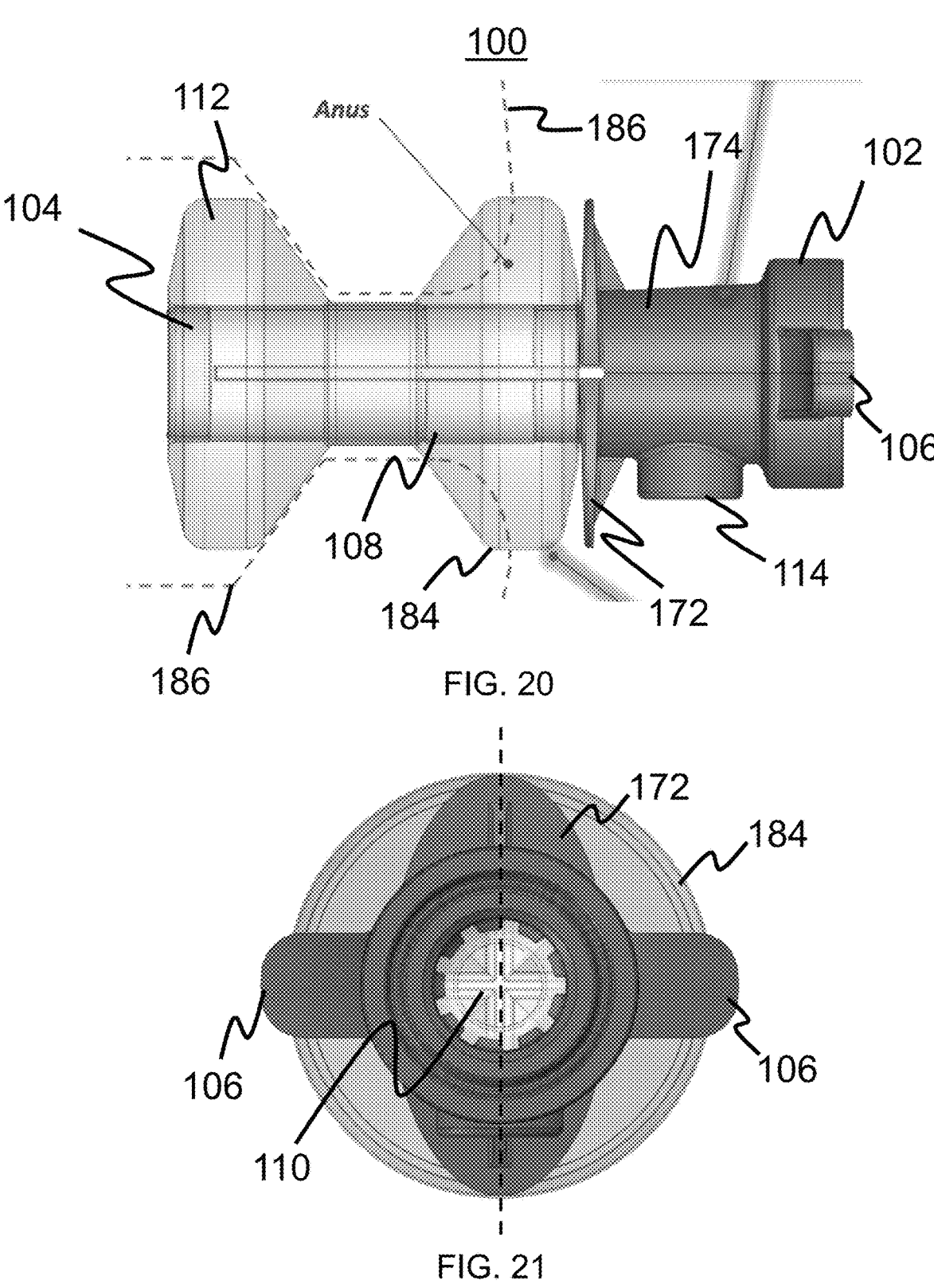
FIG. 20 is a side view illustration of the slidable mount with two expandable balloons, according to one embodiment of the invention.
FIG. 21 is a rear view illustration of the slidable mount with two expandable balloons, according to one embodiment of the invention.

FIG. 20 is a side view illustration of the slidable mount with the second expandable balloon 184, illustrating the position of the plug with respect to the anatomical outline of the anal cavity 186. The second expandable balloon 184 is shown as it fits into the anal cavity to create a seal on the outer surface of the anus, while the first balloon 112 is inflated within the rectum on the interior side of the anus in order to create a retaining force and seal to secure the plug from being moved in either direction during an endoscopic procedure. FIG. 21 is a rear view illustration of the slidable mount 172 illustrating the relative position and shape of the second expandable balloon 184, slidable mount 172 and support tabs 106. The dotted line represents the intergluteal axis.

Figure 22:
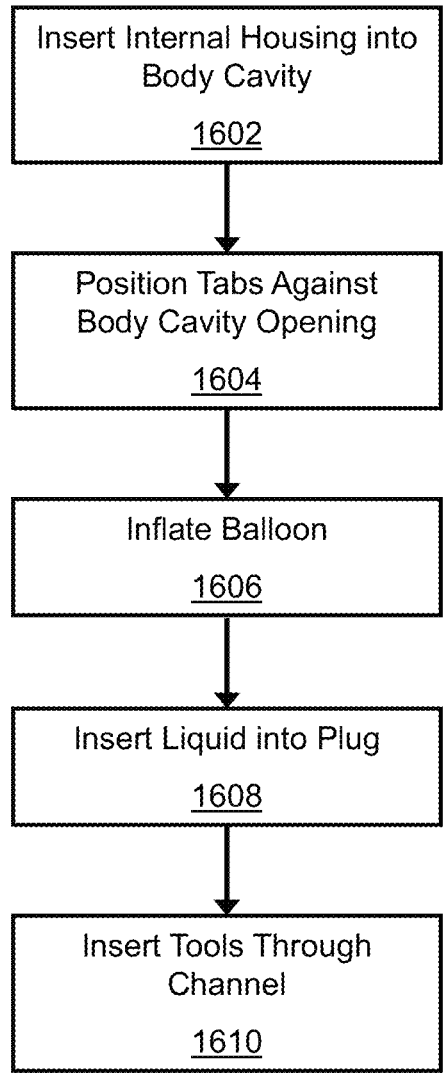
FIG. 22 is a flow diagram illustrating an example process for inserting the endoscopic plug into a body orifice, according to an embodiment of the invention.

Regardless of the embodiment utilized, the endoscopic plug may be secured within the body cavity in accordance with the steps illustrated in the flow diagram in FIG. 22. In a first step 1602, the internal housing is inserted through the body cavity opening and into the body cavity itself. In step 1604, the support tabs and tapered edge of the external housing are secured against the exterior surrounding tissue of the body cavity opening. In step 1606, the balloon is inflated by introduction of pressurized air through the inflation tube. Although not part of the method of securing the plug itself, the method may further include the steps of inserting liquid through the plug and into the body cavity (1608) and inserting one or more tools into the channel (1610) for performing an endoscopic procedure. It is noted that while the device is primarily described for performing WAE, the plug may be suitable for performing other endoscopic procedures.

The above description of the disclosed embodiments is provided to enable any person skilled in the art to make or use the invention. Various modifications to these embodiments will be readily apparent to those skilled in the art, and the generic principles described herein can be applied to other embodiments without departing from the spirit or scope of the invention. Thus, it is to be understood that the description and drawings presented herein represent a presently preferred embodiment of the invention and are therefore representative of the subject matter which is broadly contemplated by the present invention. It is further understood that the scope of the present invention fully encompasses other embodiments that may become obvious to those skilled in the art and that the scope of the present invention is accordingly not limited.

What is claimed is:

1. An endoscopic plug, comprising:
an external housing disposed external to a body cavity opening, the external housing including:
a sealed opening at a proximal end of the external housing for insertion of one or more tools into a primary channel disposed therein;
a port connector extending outward from a side opening at the proximal end of the external housing;
a pair of support tabs disposed on an external surface of the external housing and extending radially outward from the sealed opening in opposite directions, wherein the pair of support tabs are distal to the port connector, and wherein the pair of support tabs are shaped to fit against an intergluteal cleft of the body cavity opening;
an internal housing disposed within a body cavity and connected with the external housing such that the primary channel continues through the internal housing to a distal opening for insertion of the one or more tools into the body cavity;
wherein the internal housing includes an expandable balloon disposed around an outer surface of the internal housing; and
wherein the internal housing includes a secondary channel disposed within a housing wall for passage of air from an external source to the expandable balloon.

2. The endoscopic plug of claim 1, wherein the external surface of the distal end of the external housing is tapered from the at least one support tab in a direction of the body cavity opening.

3. The endoscopic plug of claim 1, further comprising at least one fluid connector for managing fluid in the body cavity through the endoscopic plug.

4. The endoscopic plug of claim 1, further comprising a slidable external mount disposed around the external housing for securing the plug against an external surface of an anal cavity.

5. A method of inserting an endoscopic plug for water-aided endoscopy, comprising:
inserting a semi-flexible tubing into a body cavity opening, the tubing defining a primary channel and having an expandable balloon annularly disposed thereon in a deflated configuration;
positioning a pair of support tabs, which extend outward in opposing directions from a distal end of an external housing and which are distal to a port connector extending outward from a side opening at the proximal end of the external housing, against an intergluteal cleft of the body cavity opening to seal the external housing into the body cavity opening; and
inflating the expandable balloon into an inflated configuration to create an internal seal between the expandable balloon and a body cavity wall.

6. The method of claim 5, further comprising a tapered surface disposed annularly on the external surface of the external housing and tapering toward the tubing to further seal the external housing into the body cavity opening.

7. The method of claim 5, further comprising inflating the expandable balloon by sending air through a secondary channel disposed within a wall of the tubing and in communication with the balloon and an external pressurized air source.

8. The method of claim 5, further comprising positioning the distal end of the external housing against the external surface of the body cavity opening via a slidable external mount disposed around the external housing.

\* \* \* \* \*